US007199217B2

(12) United States Patent
DiMarchi et al.

(10) Patent No.: US 7,199,217 B2
(45) Date of Patent: Apr. 3, 2007

(54) AMIDATED GLUCAGON-LIKE PEPTIDE-1

(75) Inventors: Richard Dennis DiMarchi, Carmel, IN (US); Rohn Lee Millican, Jr., Indianapolis, IN (US); Wolfgang Glaesner, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 237 days.

(21) Appl. No.: 10/450,042

(22) PCT Filed: Nov. 30, 2001

(86) PCT No.: PCT/US01/43167

§ 371 (c)(1),
(2), (4) Date: Jun. 10, 2003

(87) PCT Pub. No.: WO02/48192

PCT Pub. Date: Jun. 20, 2002

(65) Prior Publication Data

US 2004/0132647 A1  Jul. 8, 2004

Related U.S. Application Data

(60) Provisional application No. 60/255,251, filed on Dec. 13, 2000.

(51) Int. Cl.
*C07K 14/605* (2006.01)
(52) U.S. Cl. .................. 530/324; 530/308; 514/12
(58) Field of Classification Search ............... 530/324, 530/399, 308; 514/12
See application file for complete search history.

(56) References Cited

U.S. PATENT DOCUMENTS

| 4,347,374 | A | 8/1982 | Kollonitsch et al. |
| 5,118,666 | A | 6/1992 | Habener |
| 5,120,712 | A | 6/1992 | Habener |
| 5,545,618 | A | 8/1996 | Buckley et al. |
| 5,705,483 | A | 1/1998 | Galloway et al. |
| 5,977,071 | A | 11/1999 | Galloway et al. |
| 6,133,235 | A | 10/2000 | Galloway et al. |
| 6,284,727 | B1 | 9/2001 | Kim et al. |
| 6,388,053 | B1 | 5/2002 | Galloway et al. |
| 6,410,513 | B1 | 6/2002 | Galloway et al. |
| 2004/0053370 | A1* | 3/2004 | Glaesner et al. ............ 435/69.7 |

FOREIGN PATENT DOCUMENTS

| EP | 0 619 322 | 2/1994 |
| EP | 0 733 644 | 9/1996 |
| WO | WO 91/11457 | 8/1991 |
| WO | WO 92/18531 | 10/1992 |
| WO | WO 93/18786 | 9/1993 |
| WO | WO 95 05848 | 3/1995 |
| WO | WO 93/25579 | 12/1995 |
| WO | WO 87 06941 | 11/1997 |
| WO | WO 99 30731 | 6/1999 |
| WO | WO 00 01727 | 1/2000 |
| WO | WO 02 10195 | 2/2002 |

OTHER PUBLICATIONS

Altman, J., et al., "An Improved Synthesis of L-Homhistidine," Synthetic Commun., 19 (11 & 12) : 2069-2076, 1989.
Ananthanarayanan, V.S., et al. "$Ca^{2+}$Binding and Ionophoretic Properties of Peptide Hormones: Studies on Insulin and Glucagon," Molecular Biology Cell (Supp) 3, 250A, 1992.
Clark, B. A., et al, "Effect of Glucose, Insulin, and Hypertonicity on Atrial Natriuretic Peptide Levels in Man." Database Medline Online, US National Library of Medicine, Bethesda, MD, XP002214279, Clinical and Experimental, vol. 42, No. 2, Feb. 1993 (1193-02), pp. 224-228, abstract.
Epand, R.M., "Cation-Induced Conformational Change in Glucagon," Molecular Pharmacology, 22:105-108, 1982.
Galloway, J.A., "Treatment of NIDDM With Insulin Agonists or Substitutes," Diabetes Care, 13: 1209-1239, 1990.
Galloway, J.A., "Insulin Agonist Therapy: A Challenge for the 1990s," Clinical Therapeutics, 12:460-472, 1990.
Gutniak, M, et al., "Antidiabetogenic Effect of Glucagon-Like Peptide-I (7-36) Amide in Normal Subjects and Patients with Diabetes Mellitus," New England Journal of Medicine, 326 (20) : 1316-1322, 1992.
"Handbook of Experimental Pharmacology," Springer-Verlag, Hasselblatt, et al., (Eds.), 32 (2) :729-777, 1975.
Holz, G. G., et al., Pancreatic Beta-Cells Are Rendered Glucose-Competent by the Insulinotropic Hormone Glucagon-Like Peptide 1(7-37) , Nature, 361:362-365, 1993.
Ishikawa, Hirokazu, et al, "Large-Scale Preparation of Recombinant Human Calcitonin from a Multimeric Fusion Protein Produced in *Escherichia coli*" XP 002214281 & Journal of Bioscience and Bioengineering, 87 (3), 296-301, 1999, abstract.
Komatsu, R., et al., "Glucagonostatic and Insulinotropic Action of Glucagonlike Peptide 1-(7-36)-Amide," Diabetes, 38:902-905, 1989.
Levine-Pinto, H. et al., "Specific and Direct Fluorinatii Histidine-Containing Peptide," Biochemical, Biophysical Research Communications, 103(4) :1121-1130, 1981.
Mentlein, R., et al., "Dipeptidyl-peptidase IV Hydrolyses Gastric Inhibitory Polypeptide, Glucagon-like Peptide-1 (7-36Amide, Peptide Histidine Methionine and is Responsible for their Degradation in Human Serum," Eur. J. Biochem, 214:829-835, 1993.
Mojsov, S., "Structural Requirements for Biological Activity of Glucagon-like Peptide-I," Int. J. Peptide Protein Res., 40:333-343, 1989.
Nauck, M.A., et al., "Preserved Incretin Activity of Glucagon-like Peptide 1[7-36 Amide] but Not of Synthetic Human Gastric Inhibitory Polypeptide in Patients with Type-2 Diabetes Mellitus," J. Clinical Invest., 91:301-307, 1993.

(Continued)

*Primary Examiner*—David Lukton
(74) *Attorney, Agent, or Firm*—Gregory A. Cox; Mark J. Stewart

(57) ABSTRACT

The present invention encompasses a GLP-1 analog and compositions and formulations thereof useful for the treatment of hyperglycemia and other various diseases and conditions in mammals.

1 Claim, No Drawings

OTHER PUBLICATIONS

Nauck, M.A., et al., Normalization of Fasting Hyper-glyeaemia by Exogenous Glucagon-like Peptide 1 (7-36 amide) in Type 2 (non-insulin-dependent) Diabetic Patients Diabetologia, 36:741-744, 1993.

O'Donnell, J.J., et al., Synthesis of A-Methylhistidine By Catalytic Phase-Transfer Alkylations, Synthetic Communication, 19 (7 & 8): 1157-1165, 1989.

Orskov, C., "Glucagon-Like Peptide-1: A New Hormone of the Entero-insular Axis," Diabetologia, 35: 701-711, 1992.

Orskov, C., et al., "Complete Sequences of Glucagon-like Peptide-1 from Human and Pig Small Intestine," Journal of Biological Chemistry, 264 (22) :12826-12829, 1989.

Owa, T., et al., "An Efficient Synthesis of Erythro-β-Hydroxy-L-histidine, the Pivotal Amino Acid of Bleomycin-Fe (II) -$0_2$ Complex[1,]" Chem. Letters: 873-874, 1988.

Pridal, Lone, et al, "Absorption of Glucagon-like Peptide-1 Can Be Protracted by Zinc or Protamine" XP 002214282; International Journal of Pharmaceuticals, 136:53-59, 1996.

Suzuki, S, et al, "Comparison of the Effects of Various Carboxyl-Terminal and Amino-Terminal Fragment Peptides of Glucagon-Like Peptide-1 on Insulin and Glucagon Release from the Isolated Perfused Rat Pancreas." XP 002214280 & Endocrinology, vol. 125, No. 6, 3109-3114, 1989.

Thorens, B., et al., *"Perspectives in Diabetes*: Glucagon-Like Peptide-1 and the Control of Insulin Secretion in the Normal State and in NIDDM," Diabetes, 42:1219-1225, 1993.

\* cited by examiner

SEQUENCE LISTING

```
<160> NUMBER OF SEQ ID NOS: 3

<210> SEQ ID NO 1
<211> LENGTH: 31
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(2)
<223> OTHER INFORMATION: Xaa at position 2 is Val;
<220> FEATURE:
<221> NAME/KEY: MISC_FEATURE
<222> LOCATION: (16)..(16)
<223> OTHER INFORMATION: Xaa at position 16 is Gly;
<220> FEATURE:
<221> NAME/KEY: MISC_FEATURE
<222> LOCATION: (21)..(21)
<223> OTHER INFORMATION: Xaa at position 21 is Glu;
<220> FEATURE:
<221> NAME/KEY: MISC_FEATURE
<222> LOCATION: (24)..(24)
<223> OTHER INFORMATION: Xaa at position 24 is Ala;
<220> FEATURE:
<221> NAME/KEY: MOD_RES
<222> LOCATION: (31)..(31)
<223> OTHER INFORMATION: AMIDATION
<220> FEATURE:
<221> NAME/KEY: MISC_FEATURE
<222> LOCATION: (31)..(31)
<223> OTHER INFORMATION: Xaa at position 31 is Gly.

<400> SEQUENCE: 1

His Xaa Glu Gly Thr Phe Thr Ser Asp Val Ser Ser Tyr Leu Glu Xaa
1               5                   10                  15

Gln Ala Ala Lys Xaa Phe Ile Xaa Trp Leu Val Lys Gly Arg Xaa
            20                  25                  30

<210> SEQ ID NO 2
<211> LENGTH: 31
<212> TYPE: PRT
<213> ORGANISM: Homo sapiens

<400> SEQUENCE: 2

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30
```

```
<210> SEQ ID NO 3
<211> LENGTH: 31
<212> TYPE: PRT
<213> ORGANISM: Artificial Sequence
<220> FEATURE:
<223> OTHER INFORMATION: Synthetic construct

<400> SEQUENCE: 3

His Val Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
                20                  25                  30
```

AMIDATED GLUCAGON-LIKE PEPTIDE-1

This is the national phase application, under 35 U.S.C. § 371, for PCT/US01/43167, filed Nov. 30, 2001, which claims the benefit of U.S. Provisional Application No. 60/255,251, filed Dec. 13, 2000.

BACKGROUND OF THE INVENTION

Glucagon-Like Peptide 1 (GLP-1) is a 37 amino acid peptide that is secreted by the L-cells of the intestine in response to food ingestion. It has been found to stimulate insulin secretion (insulinotropic action), thereby causing glucose uptake by cells and decreased serum glucose levels (see, e g., Mojsov, S., *Int. J. Peptide Protein Research*, 40:333–343 (1992)). These and other effects make GLP-1 an attractive candidate for the treatment of type 2 diabetes.

Thus far, however, efforts to commercially develop a GLP-1 drug candidate have been hampered by numerous obstacles. For example, the development of native GLP-1 compounds has not been feasible because they are rapidly degraded by endogenous proteases and thus, have an extremely short in vivo half-life. Although analogs with longer half-lives have been studied, these analogs have been difficult to develop commercially due to stability problems encountered during the manufacturing process.

One particular analog that has been studied is $Val^8$-GLP-1(7–37)OH. See U.S. Pat. No. 5,977,071. This analog has a potency similar to that of the truncated native GLP-1 peptides GLP-1(7–36)$NH_2$ and GLP-1(7–37)OH but has a longer circulating half-life. $Val^8$-GLP-1(7–37)OH, however, exists in at least two different forms. The first form is physiologically active and dissolves readily in aqueous solution whereas the second form is substantially insoluble in water at physiological pH and is inactive. Further, $Val^8$-GLP-1(7–37)OH has a tendency to aggregate and convert to an inactive insoluble form during manufacturing. Thus, efforts to improve the properties of this compound have continued. Discovery efforts have focused on improving the stability of the compound in the context of large scale manufacturing as well as formulation development without compromising the biological activity.

The present invention encompasses a $Val^8$-GLP-1 analog having such improved properties. The invention encompasses the discovery that an amidated form of $Val^8$-GLP-1 (7–37)OH known as $Val^8$-GLP-1(7–37)$NH_2$ has increased in vitro potency compared to $Val^8$-GLP-1(7–37)OH (the acid form) and has superior stability properties that facilitate large-scale manufacturing and make it an ideal candidate to formulate as a solution for continuous infusion or as a crystal suspension for subcutaneous administration.

Although native GLP-1 is amidated in vivo, there has been no motivation to study amidated analogs because both native isoforms appear to have identical biological effects and amidated peptides are perceived as more difficult to make biosynthetically. In addition, unlike the amidated analog encompassed by the present invention, amidation of the native molecule actually involves replacement of the C-terminal glycine-OH with $NH_2$ resulting in GLP-1(7–36)$NH_2$. Further, the corresponding $Val^8$-GLP-1(7–36)$NH_2$ analog, disclosed in U.S. Pat. No. 6,133,235, actually turns out to be slightly less potent than the acid form.

Thus, it is surprising that $Val^8$-GLP-1(7–37)$NH_2$ has increased stability as a formulated compound as well as increased stability in the context of manufacturing processes over the acid form of the analog. Even more surprising is the increased potency compared to the acid form or the truncated amide form of the analog.

SUMMARY OF THE INVENTION

The present invention comprises a peptide having the sequence represented in Formula I (SEQ ID NO:1).

```
                                  Formula I (SEQ ID NO: 1)
 7   8   9  10  11  12  13  14  15  16  17
His-Xaa-Glu-Gly-Thr-Phe-Thr-Ser-Asp-Val-Ser- 18  19  20  21  22  23  24  25  26  27  28
Ser-Tyr-Leu-Glu-Xaa-Gln-Ala-Ala-Lys-Xaa-Phe- 29  30  31  32  33  34  35  36  37
Ile-Xaa-Trp-Leu-Val-Lys-Gly-Arg-R
``` wherein:
Xaa at position 8 is Val; Xaa at position 22 is Gly;
Xaa at position 27 is Glu; Xaa at position 30 is Ala;
and R is Gly-$NH_2$;

The present invention also comprises a solution formulation of the peptide corresponding to SEQ ID NO:1. The present invention further comprises crystals of the peptide corresponding to SEQ ID NO:1 as well as pharmaceutical compositions of such crystals.

DETAILED DESCRIPTION OF THE INVENTION

The three-letter abbreviation code for amino acids used in this specification conforms with the list contained in Table 3 of Annex C, Appendix 2 of the PCT Administrative Instructions and with 37 CFR § 1.822(d)(1)(2000).

It has now been found that $Val^8$-GLP-1(7–37)$NH_2$ shows a markedly decreased propensity to aggregate in solution compared with $Val^8$-GLP-1(7–37)OH yet can still be crystallized to provide extended time action similar to $Val^8$-GLP-1(7–37)OH. Further, $Val^8$-GLP-1(7–37)$NH_2$ has an in vitro potency that is approximately 1.2-fold greater than $Val^8$-GLP-1(7–37)OH.

As accustomed in the art, the N-terminal residue of a GLP-1 related peptide is represented as position 7. Thus, the amino acid sequence of the naturally occurring human GLP-1 related peptide designated GLP-1(7–37)OH is:

```
                                        (SEQ ID NO: 2)
 7   8   9  10  11  12  13  14  15  16  17
His-Ala-Glu-Gly-Thr-Phe-Thr-Ser-Asp-Val-Ser- 18  19  20  21  22  23  24  25  26  27  28
Ser-Tyr-Leu-Glu-Gly-Gln-Ala-Ala-Lys-Glu-Phe- 29  30  31  32  33  34  35  36  37
Ile-Ala-Trp-Leu-Val-Lys-Gly-Arg-Gly
```

$Val^8$-GLP-1(7–37)$NH_2$ is GLP-1(7–37)OH wherein Ala at position 8 has been substituted with Val and Gly at position 37 has been amidated.

The amino acid sequence of $Val^8$-GLP-1(7–37)OH is:

```
                                        (SEQ ID NO: 3)
 7   8   9  10  11  12  13  14  15  16  17
His-Val-Glu-Gly-Thr-Phe-Thr-Ser-Asp-Val-Ser- 18  19  20  21  22  23  24  25  26  27  28
Ser-Tyr-Leu-Glu-Gly-Gln-Ala-Ala-Lys-Glu-Phe- 29  30  31  32  33  34  35  36  37
Ile-Ala-Trp-Leu-Val-Lys-Gly-Arg-Gly
```

The word "crystal" in the present specification refers to a solid material comprising a peptide in which the particles making up the solid have a definite form or structure. Particles lacking such form or structure are referred to as "amorphous." Words used in the present specification to describe crystals include, in order of increasing crystal quality; 1) "microcrystals," which are small crystals possessing a definite but essentially non-linear form or structure, 2) "stars" or "clusters," which are distinct crystals fused at or emanating from a central core and which may contain amorphous material in addition to crystalline material, and 3) "rods," "needles," or "plates" which are individual crystals possessing a distinctive form or structure consistent with their name.

The term "thin plate crystals" refers to individual peptide crystals having an apparent orthorhombic structure in which the three axes of the crystals have disparate lengths. The thin plate crystals of the present invention generally have a thickness of about 0.5 µm to about 3.0 µm, a width of about 3 µm to about 10 µm and a length of about 10 µm to about 100 µm. Under the microscope thin plate crystals may appear orthorhombic but the actual angles between the axes may or may not be 90°.

The word "stable" used in the present specification refers to a composition in which both the chemical stability and physical stability of the composition remain at an acceptable level over time. The word "chemical" used in conjunction with stability of a peptide composition refers to covalent modifications or alterations of the peptide. The word "physical" used in conjunction with stability of a peptide composition refers to the molecular conformation, solubility or solid form properties of the peptide. By way of illustration, peptide crystal compositions in which the crystals quickly clump into large aggregates or dissolve into the liquid medium exhibit unsatisfactory physical stability.

The word "pharmaceutical" used in the present specification in reference to a peptide composition means it contains a peptide useful for treating a disease or condition. For example, the peptide Val$^8$-GLP-1(7–37)NH$_2$ described in the present invention is useful in treating humans and other mammals who have Type 2 diabetes.

The word "treating" refers to the management and care of a patient for the purpose of combating a disease, condition, or disorder and includes the administration of crystals, a pharmaceutical composition thereof, or a pharmaceutically-acceptable solution formulation to prevent the onset of the symptoms or complications, alleviating the symptoms or complications, or eliminating the disease, condition or disorder. Treating diabetes therefore includes the maintenance of physiologically desirable blood glucose levels in patients in need thereof.

For the convenience and safety of patients being treated, pharmaceutical compositions of the present invention also contain a pharmaceutically acceptable preservative. A "pharmaceutically acceptable preservative" refers to a chemical that is compatible with and suitable for pharmaceutical use in humans and that is added to a peptide composition to prevent or inhibit the growth of micro-organisms. The term "phenolic preservative" as used herein refers to a pharmaceutically acceptable preservative containing a phenolic moiety and includes phenol, m-cresol, methylparaben and mixtures thereof. Utilizing a pharmaceutically acceptable preservative in a peptide composition allows a patient to conveniently make multiple withdrawals of the composition from the same container, such as a vial or cartridge, over an extended period of time.

The word "buffer" refers to a chemical compound in a composition that minimizes changes in hydrogen ion concentration that would otherwise occur as a result of a chemical reaction and includes, but is not limited to, TRIS, maleate, phosphate, succinate, glycylglycine, adipate, citrate, and acetate.

The term "TRIS" refers to 2-amino-2-hydroxymethyl-1,3-propanediol, and any pharmaceutically acceptable salt thereof. The free base and the hydrochloride form are two common forms of TRIS. TRIS is also known in the art as trimethylol aminomethane, tromethamine and tris(hydroxymethyl)aminomethane.

The word "maleate" refers to maleic acid, which has the chemical formula HOOCCH:CHCOOH, and pharmaceutically acceptable salt forms such as sodium maleate and potassium maleate.

The word "succinate" refers to succinic acid, which has the chemical formula $CO_2H(CH_2)_2CO_2H$, and pharmaceutically acceptable salt forms such as sodium succinate and potassium succinate.

The word "adipate" refers to adipic acid, which has the chemical formula $CO_2H(CH_2)_4CO_2H$, and pharmaceutically acceptable salt forms such as sodium adipate and potassium adipate.

The word "glycylglycine" refers to the dipeptide Gly-Gly, the free base form of Gly-Gly and pharmaceutically acceptable salt forms such as glycylglycine hydrochloride.

The word "ethanol" is synonymous with ethyl alcohol and refers to the chemical $CH_3CH_2OH$.

The word "isopropanol" is synonymous with isopropyl alcohol and refers to the chemical $(CH_3)_2CHOH$.

The term "tonicity agent" refers to a non-volatile chemical compound that modifies the osmotic pressure of a solution or suspension composition and includes sodium chloride, other salts, glycerin and mannitol.

"TCR" stands for "Temperature Cycling and Resuspension" and refers to the automated test of pharmaceutical compositions involving temperature cycling and physical resuspension described herein as Method 2. The "Modified TCR Test" refers to the test described herein as Method 3.

The symbol "%" is equivalent to the word "percent" and, as used herein in reference to a volume of a specified liquid within a larger liquid composition or added to a liquid composition, means the actual volume of the specified liquid divided by the total volume of the combined composition after the specified liquid is added, multiplied by 100.

As noted, the present invention comprises a peptide, known as Val$^8$-GLP-1(7–37)NH$_2$, having the sequence represented in formula I (SEQ ID NO:1).

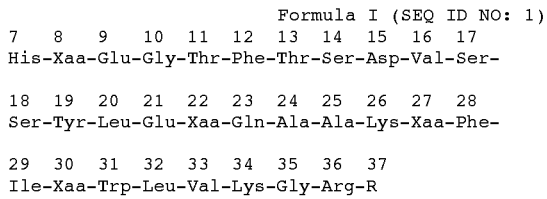

```
                                 Formula I (SEQ ID NO: 1)
   7   8   9   10  11  12  13  14  15  16  17
   His-Xaa-Glu-Gly-Thr-Phe-Thr-Ser-Asp-Val-Ser- 18  19  20  21  22  23  24  25  26  27  28
   Ser-Tyr-Leu-Glu-Xaa-Gln-Ala-Ala-Lys-Xaa-Phe- 29  30  31  32  33  34  35  36  37
   Ile-Xaa-Trp-Leu-Val-Lys-Gly-Arg-R
``` wherein:
Xaa at position 8 is Val; Xaa at position 22 is Gly; Xaa at position 27 is Glu; Xaa at position 30 is Ala; and R is Gly-NH$_2$;

Val$^8$-GLP-1(7–37)NH$_2$ may be prepared by various methods. For example, the peptide may be chemically synthesized by solution-phase, solid-phase or semi-synthetic methods (see Example 1). Alternatively, the peptide may be prepared biosynthetically using recombinant DNA technology in modified bacteria, yeast, mammalian cells or in transgenic plants or animals and then amidated using a transpeptidation reaction (see Example 2).

Transpeptidation is a reaction that uses a proteolytic enzyme to both cleave a peptide bond to remove an amino acid residue(s) from a substrate peptide and subsequently form a new peptide bond between the substrate and la new amino acid residue. Thus, $Val^8$-GLP-1(7–37)OH can be prepared biosynthetically and then converted to $Val^8$-GLP-1(7–37)$NH_2$ by removing the C-terminal glycine and replacing it with an amidated-glycine (Gly-$NH_2$) residue. This can be achieved by adding water miscible organic solvents to the reaction mixture and having a large molar excess of the amidated amino acid residue in solution. For example, $Val^8$-GLP-1(7–37)OH can be converted to $Val^8$-GLP-1(7–37)$NH_2$ using trypsin-mediated or carboxypeptidase Y-mediated transpeptidation. Trypsin is preferred because of its selectivity for basic amino acid residues such as lysine and arginine and the penultimate amino acid residue at the C-terminal end of $Val^8$-GLP-1(7–37)OH is arginine. To prevent trypsin from digesting $Val^8$-GLP-1(7–37)OH at each of the two internal lysines, these lysines can be modified to prevent digestion. For example, the lysines can be acylated using citriconic anhydride in an aqueous buffered solution to temporarily protect the lysine residues from trypsin digestion. Further this type of a reaction caps the N-terminal amino group of the peptide. Once the protected $Val^8$-GLP-1(7–37)OH molecule is treated with trypsin, the acyl groups can be removed.

The $Val^8$-GLP-1(7–37)$NH_2$ peptide has slightly increased in vitro activity compared to $Val^8$-GLP-1(7–37)OH and has a substantially reduced tendency to aggregate in solution. $Val^8$-GLP-1(7–37)$NH_2$ and $Val^8$-GLP-1(7–37)OH were analyzed with respect to their potential to aggregate in solution (see Example 3). The peptides in solution were stirred at elevated temperature in a suitable buffer while recording turbidity at 350 nm as a function of time. Time to the onset of aggregation was measured to quantify the potential of each GLP-1 molecule to aggregate under these stressed conditions. $Val^8$-GLP-1(7–37)$NH_2$ had an aggregation time of approximately 23 hours at 37° C. compared to 1 hour for $Val^8$-GLP-1(7–37)OH at 37° C. Thus, $Val^8$-GLP-1(7–37)$NH_2$ is less likely to aggregate and convert to an inactive insoluble form during manufacturing and will have superior stability as a formulated solution or crystal suspension.

The present invention also encompasses a pharmaceutically-acceptable solution formulation and a lyophilized formulation that can be reconstituted as a solution comprising $Val^8$-GLP-1(7–37)$NH_2$. These types of formulations are most useful for continuous intravenous (i.v.) infusion of $Val^8$-GLP-1(7–37)$NH_2$. Continuous infusion means continual and substantially uninterrupted administration of a solution for a specified period of time. Such formulations are also useful when a bolus injection is desired. A bolus injection is the injection of a drug in a defined quantity at once. Due to the relatively short half-life of $Val^8$-GLP-1(7–37)$NH_2$ when administered as a solution, it is preferred that a solution of this molecule be administered by continuous infusion.

It is known that GLP-1 molecules have effects beyond glucose normalization in diabetics. For example, GLP-1 has been shown to reduce the mortality and morbidity associated with stroke and myocardial infarction as well as effect catabolic changes that occur after surgery. See WO 98/08531, WO 98/08873, and WO 00/16797. Post-surgical patients as well as patients who have suffered an MI or stroke generally spend some time in the hospital. Thus, a solution formulation or a lyophilized formulation that could be reconstituted is particularly suitable for i.v. administration in a hospital setting.

A solution formulation is comprised of $Val^8$-GLP-1(7–37)$NH_2$ dissolved in an aqueous solution. Such formulation has the appropriate stability and is suitable for intravenous administration. Preferably, the solution formulation is comprised of a pharmaceutically-acceptable buffer, and the pH adjusted to maintain solubility and provide acceptable stability. Optionally, one or more pharmaceutically-acceptable preservatives such as a phenolic preservative may be added. Meta-cresol and phenol are preferred pharmaceutically-acceptable preservatives. One or more pharmaceutically-acceptable salts may also be added to adjust the ionic strength or tonicity. One or more excipients may be added to further adjust the isotonicity of the formulation. Glycerin is an example of an isotonicity-adjusting excipient. One or more excipients may be added to control non-specific adsorption of the protein to the administration device or equipment (e.g., tubing, i.v. bag). Examples of such excipients include but is not limited to human serum albumin and detergents.

Alternatively, $Val^8$-GLP-1(7–37)$NH_2$ can be prepared as a lyophilized product and then reconstituted before administration. A preferred lyophilized product is comprised of $Val^8$-GLP-1(7–37)$NH_2$ and a bulking agent such as mannitol, trehalose, raffinose, and sucrose. The preferred concentration of $Val^8$-GLP-1(7–37)$NH_2$ in the lyophilized product is between about 0.5 mg and about 20 mg, preferably between about 1 mg and about 10 mg, most preferably between about 1 mg and about 5 mg. Prior to lyophilization and upon reconstitution, it is preferable to maintain the pH range between about 6 and about 10, preferably between about 6.5 and about 8 and most preferably between about 7 and about 7.5.

Accordingly, upon lyophilization, the product optionally comprises a pharmaceutically acceptable buffer. Preferred buffer systems include Tris, citrate, phosphate, and maleate based buffers. The buffering capacity of the lyophilized product may be used to control the pH of the i.v. solution to maximize stability of the peptide. For example, the pH of standard 0.9% NaCl which is unbuffered and has a pH in the range of 4.5 to 7.0 can be raised to a pH range where the peptide is stabilized. Further, upon lyophilization, the product optionally comprises a salt to generate ionic strength. Representative salts include, but are not limited to, potassium chloride (KCl) and sodium chloride (NaCl).

The lyophilized product is reconstituted with the appropriate diluent such as sterile water or sterile saline. Preferably the diluent is compatible with whatever i.v. fluid a patient may be receiving in the hospital such that if injected directly into an i.v. line or i.v. bag already attached to a patient, $Val^8$-GLP-1(7–37)$NH_2$ does not precipitate or aggregate and remains soluble and stable until delivery to the patient occurs. Typical i.v. solutions are represented in Table I.

| Solution | $Na^+$ | $K^+$ | $Ca^{+2}$ | $Cl^-$ | Lactate | $PO_4^{-3}$ | $Mg^{+2}$ |
|---|---|---|---|---|---|---|---|
| Normal Saline (NS) | 154 | 0 | 0 | 154 | 0 | 0 | 0 |
| 0.2% NS | 31 | 0 | 0 | 31 | 0 | 0 | 0 |
| 3% NaCl | 513 | 0 | 0 | 513 | 0 | 0 | 0 |
| Ringer's Lactate (LR) | 130 | 4 | 3 | 109 | 28 | 0 | 0 |

Infusion rates for the solution formulations of the present invention should be such that $Val^8$-GLP-1(7–37)$NH_2$ concentrations in the serum remain in the therapeutic range during a course of treatment. Preferably, not more than a total amount of about 5 mg of $Val^8$-GLP-1(7–37)$NH_2$ should be administered within a 24 hour period. Even more preferably, not more than a total amount between about 1 mg and about 3 mg should be administered within a 24 hour period. Most preferably a total dose of about 1 mg should be administered per 24 hour period.

The present invention also encompasses crystals comprising a peptide of Formula I (SEQ ID NO:1) as well as pharmaceutical compositions comprising such crystals. A pharmaceutical composition as used herein is comprised of a suspension of peptide crystals.

Thin plate crystals described herein have the appearance of orthorhombic crystals in which the three axes have disparate lengths. Although the lengths of the axes are not to be construed as limited to specific dimensions, the thin plate crystals of the present invention generally have a thickness of about 0.5 µm to about 3.0 µm, a width of about 3 µm to about 10 µm and a length of about 10 µm to about 100 µm. Under the microscope thin plate crystals may appear orthorhombic but the actual angles between the axes may or may not be 90°.

In addition to their surface charge, the shape and dimensions of thin plate crystals are important properties that can provide a slow sedimentation rate in a pharmaceutical composition of the present invention. Preferably, the thickness, width and length of the peptide crystals are about 0.5–1.5 µm, about 3–8 µm, and about 15–80 µm, respectively. More preferably, the thickness, width and length of the crystals are about 0.8–1.2 µm, about 4–6 µm and about 20–60 µm, respectively. Most preferably, the thickness, width and length of the crystals are about 1 µm, about 5 µm and about 30–50 µm, respectively. Analysis of the sedimentation rates and volumes of pharmaceutical compositions comprising these peptide crystals is performed as described in Method 1. Preferably the sedimentation volume after 24 hours is between about 53% and about 72% of total volume.

The pharmaceutical compositions of the present invention comprise crystals of $Val^8$-GLP-1(7–37)$NH_2$, zinc, an alcohol selected from the group consisting of ethanol and isopropanol, a buffer, a pharmaceutically acceptable preservative, and a pH between about 6.0 and about 8.5. Compositions of $Val^8$-GLP-1(7–37)$NH_2$ comprising zinc and alcohol are further stabilized in the presence of glycine and buffer selected from the group consisting of TRIS and maleate. Additional pharmaceutically acceptable excipients, such as those described in Remington's Pharmaceutical Sciences (1985) may be included in the compositions of the present invention. Preferably, such additional excipients do not affect the novel and basic characteristics of the invention. Therefore, the chemical and physical stability and the therapeutic benefit of the pharmaceutical composition are retained.

Preferably, the total peptide concentration in the compositions of the present invention is about 1.0 mg/mL to about 50 mg/mL. More preferably, the peptide concentration is about 2.0 mg/mL to about 30 mg/mL. Other ranges of preferred concentrations of peptide are about 5.0 to about 20.0 mg/mL, about 5.0 to about 10.0 mg/mL and about 2.0 mg/mL to about 8.0 mg/mL. A most preferred peptide concentration is about 6.0 mg/mL.

The compositions of the present invention comprise glycine at a concentration of about 5 mM to about 100 mM. Preferably, the glycine concentration is about 10 mM to about 50 mM. More preferably, the glycine concentration is about 20 mM to about 30 mM and more highly preferred is a glycine concentration of about 22 mM to about 24 mM. A glycine concentration of about 23 mM is most preferred.

The compositions of the present invention comprise an alcohol preferably selected from the group consisting of ethanol and isopropanol at a concentration, by total volume of the composition, of about 1% to about 10%. A preferred concentration of the alcohol in the compositions is about 2% to about 6% by volume. More preferred is an alcohol concentration of about 4%. A preferred alcohol is ethanol.

The compositions of the present invention comprise zinc at a concentration of about 0.2 moles to about 2.5 moles per mole of the peptide. The zinc present in the compositions is generally in the form of a zinc ion derived from zinc oxide or from zinc salts such as zinc chloride or zinc acetate. A preferred concentration of zinc is about 1.0 to about 2.25 moles per mole of the peptide in the composition. Other ranges of preferred zinc concentrations in the compositions are about 1.1 moles to about 2.0 moles per mole of the peptide and about 1.3 moles to about 1.7 moles per mole of the peptide. A more preferred zinc concentration is about 1.5 moles per mole of the peptide.

The compositions of the present invention may comprise a tonicity agent such as sodium chloride. Other tonicity agents, such as glycerin, mannitol and salts other than sodium chloride, may also be incorporated into the compositions in addition to or in place of sodium chloride. The quantities of sodium chloride (NaCl) noted in this specification refer to the quantities of sodium chloride added to a composition at a designated point in the preparation of the composition. The NaCl quantities noted in the specification do not include sodium chloride that may form from additions of acids and bases such as NaOH and HCl that may be used for pH adjustment at various stages in the preparation of the compositions. Also, it is appreciated that when sodium chloride is added to an aqueous composition a substantial portion will exist as sodium ions and chloride ions. For ease of measurement and understanding, however, the sodium and chloride ion concentrations of the compositions will not be considered, only the quantity of sodium chloride added.

When included in a composition of the present invention, a preferred concentration of sodium chloride in the composition is about 30 mM to about 200 mM. A more preferred quantity of sodium chloride is 50 mM to about 150 mM. Other ranges of preferred sodium chloride concentration are about 80 mM to about 120 mM, about 70 mM to about 130 mM, and about 90 mM to about 130 mM. A most preferred concentration of sodium chloride in the compositions of the present invention is about 110 mM.

The compositions of the present invention may also comprise a buffer. Preferably, the buffer is selected from the group consisting of TRIS and maleate or combinations thereof.

A preferred range of concentration of TRIS in the compositions of the present invention, if TRIS is the selected buffer, is about 5 mM to about 40 mM. A more preferred range of concentration of TRIS is about 10 mM to about 20 mM. A most preferred concentration of TRIS is about 15 mM.

A preferred range of concentration of maleate in the compositions of the present invention, if maleate is the selected buffer, is about 2 mM to about 20 mM. A more preferred range of concentration of maleate is about 5 mM to about 15 mM. A most preferred concentration of maleate is about 9 mM.

The compositions of the present invention comprise a hydrogen ion concentration, or pH, which is about 6.0 to about 8.5. The preferred pH range of the pharmaceutical compositions will also depend to some extent upon the selected peptide and the selected buffer. With TRIS as the buffer, a preferred range of composition pH is about 6.5 to about 8.5. More preferred ranges of pH are about 7.0 to about 7.8, about 7.2 to about 7.8, about 7.5 to about 8.5, and about 7.0 to about 8.0. With TRIS as the buffer, a most preferred pH is about 7.5. With maleate as the buffer, a preferred range of composition pH is about 6.0 to about 7.5. More preferred ranges of pH are about 6.4 to about 7.5, about 6.4 to about 7.0, and about 6.0 to about 7.0. With maleate as the buffer, a most preferred pH is about 6.5.

The compositions of the present invention comprise a pharmaceutically acceptable preservative. Preservatives provide safety and convenience to patients using pharmaceutical compositions. Antimicrobial agents may be added to a product formulation to protect the product from accidental microbial contamination during its manufacture, shelf life and use. This protection is also important when vials or cartridges containing a composition are provided that allow multiple withdrawls of the product. Selection and efficacy of pharmaceutically acceptable preservatives may also be guided by national regulatory agencies.

For the compositions of the present invention, pharmaceutically acceptable phenolic preservatives and benzyl alcohol are preferred. Examples of such phenolic preservatives include phenol, chlorocresol, m-cresol, o-cresol, p-cresol, ethylparaben, methylparaben, propylparaben, butylparaben and thymol, and mixtures thereof. More preferred preservatives are benzyl alcohol, m-cresol, phenol, methylparaben and mixtures thereof. A most preferred preservative is m-cresol.

A preferred concentration of preservative in the compositions of the present invention is about 1.0 mg/mL to about 20.0 mg/mL. Ranges of more preferred concentrations of preservative are about 2.0 mg/mL to about 8.0 mg/mL, about 2.5 mg/mL to about 4.5 mg/mL and about 2.0 mg/mL to about 4.0 mg/mL. A most preferred concentration of preservative is about 3.0 mg/mL.

The pharmaceutical compositions of the present invention are suitable for use as a medicament for treating diabetes, hyperglycemia, obesity, or related conditions in mammals.

In order to provide safety, convenience and precise dosing in administering a suspension composition, suspended material should settle very slowly in the liquid composition, it should not compact tightly at the bottom of the container upon storage and settled material should resuspend readily with minimal swirling or agitation. For example, it is preferable that the sedimentation volume be greater than 50% after 24 hours of settling at ambient temperature.

In order to provide accurate dosing and safety to patients administering a suspension composition, the suspended material of the composition should not agglomerate or clump irreversibly after normal patient use and storage for a period of time as specified by the product label. Such agglomerated or clumped material may clog the orifice of a syringe needle or other device used to administer the composition, thereby reducing the quantity of peptide delivered. Preferably, the crystal compositions of the present invention, by visual examination, exhibit satisfactory physical stability for at least 14 days in the TCR Test and for at least 28 days in the Modified TCR Test. The TCR Test especially exaggerates storage and agitation conditions beyond that expected by normal patient use. Preferably, the crystal particles in the compositions of the present invention maintain a small size, that is, about 5 μm to about 10 μm (mean volume percent distribution), for at least 28 days in the Modified TCR Test.

Chemical degradation may also occur in peptide compositions leading to formation of compounds which have reduced potency and/or unknown side effects. Thus, in order to provide safety and full dosing to patients administering peptide pharmaceutical compositions, the level of chemical degradation occurring in the composition during patient use and storage should be kept to a minimum. It is preferable that HPLC evaluations of peptide compositions that undergo the 14 day TCR or 28 day Modified TCR Tests show less than about 2% of the peptide as chemically altered.

The optimal clinical benefits of the crystal peptide compositions of the present invention are realized when reproducible, prolonged absorption is achieved. As a corollary to this goal, adverse events resulting from dose dumping that may occur soon after administration of a composition may be avoided if the quantity of soluble peptide in the composition, which tends to be absorbed very quickly, is minimized during the typical use and storage conditions of the patient. It is preferable that the concentration of soluble peptide in the compositions of the present invention are 8 μg/mL or less after 14 days in the TCR Test or after 28 days in the Modified TCR Test. This means that less than 0.3% of the peptide becomes solubilized during the course of these tests.

For pharmaceutical compositions of peptide crystals, another aspect of physical stability is maintenance of the proper molecular conformation of the peptide. This proper conformation may be critical to delivering a molecule capable of interacting with its receptor and eliciting the desired biological response. A predominantly α-helix conformation is believed to be important in providing a soluble and, therefore, bioavailable peptide while a mostly β-sheet form is believed to be essentially insoluble and, therefore, not bioavailable. The conformation of Val$_8$-GLP-1(7–37)NH$_2$ in the pharmaceutical compositions of the present invention can be evaluated by FTIR analysis after 14 days in the TCR Test. The peptide should maintain a predominantly α-helix conformation throughout the 14-day test. Therefore, the peptide in these compositions will be maximally bioavailable after administration to a mammal.

The clinical benefits of the crystal compositions of the present invention are realized when the administered peptide is present in the mammal being treated for a prolonged period of time.

The crystals of Val$^8$-GLP-1(7–37)NH$_2$ and compositions thereof according to the present invention may be used as a medicament or in preparing a medicament for the treatment of diabetes, hyperglycemia, obesity, irritable bowel syndrome or related conditions in mammals such as humans. The present invention also provides a method of treating diabetes, hyperglycemia, obesity, irritable bowel syndrome or related conditions in mammals such as humans, which comprises administering to the mammal crystals of a selected peptide or a pharmaceutical composition thereof.

A dose of 0.001 to 5 mg of a peptide in crystals or compositions thereof per kg of body weight of a mammal may be administered parenterally to the mammal in need of such treatment. One skilled in the art will recognize that smaller or larger doses may also be operable, depending on the patient, their condition and the manner of administration. Preferred dose ranges include 0.001 to 1 mg/kg, 0.002 to 3 mg/kg, 0.005 to 2 mg/kg, 0.01 to 1 mg/kg, 0.01 to 0.1 mg/kg, 0.2 to 0.8 mg/kg, 0.8 to 3 mg/kg and 0.2 to 3 mg/kg. More preferred dose ranges include 0.001 to 1 mg/kg, 0.005 to 2 mg/kg, 0.01 to 1 mg/kg, and 0.01 to 0.1 mg/kg.

A total dose of 0.01 to 20 mg, based on the mass of the crystals or the mass of the crystals in the compositions of the present invention, may be administered parenterally to a mammal, such as a human, in need of such treatment. One skilled in the art will recognize that a smaller or larger total dose may also be operable, depending on the patient, their condition and the manner of administration. Preferred total dose ranges include 0.01 mg to 10 mg, 0.1 to 10 mg, 1 to 8 mg and 2 to 6 mg. More preferred total dose ranges are 1 to 8 mg and 2 to 6 mg.

Pharmaceutical compositions of the present invention may be administered parenterally to patients in need thereof more than once per day, once per day, once every two days, twice per week, once per week, or in other dosing regimens known to those skilled in the art. A preferred dosing regimen is administration once per day.

The claimed compositions may be administered to a patient in need thereof by a variety of parenteral delivery methods appreciated by the skilled artisan. Preferred methods include subcutaneous injection, intramuscular injection, pulmonary administration, buccal, nasal, or transdermal delivery, and delivery by internal or external pump. More preferred delivery methods are subcutaneous and intramuscular injection. When injected, syringes or cartridges employing needles or needle-less devices well known in the art may be employed.

The compositions of the present invention are preferably prepared as described herein. The first step in this process is dissolving a selected peptide in a glycine-free solution at a pH of about 9.5 to about 11.5. This "alkaline normalization" step appears to reduce the content of β-sheet conformation in the peptide and enhance the α-helix conformation that is important for solubility and bioavailability. This step also serves to maintain the peptide in a preferred α-helix conformation prior to the subsequent process step. This key step thus "normalizes" variation in bulk lots of the peptide into a more reproducible, homogenous solution.

Preferably, the peptide concentration in the alkaline normalization solution is greater than 5 mg/mL. More preferably, the peptide concentration is about 10 mg/mL to about 30 mg/mL. Other ranges of preferred concentration of dissolved peptide are about 5 mg/mL to about 25 mg/mL, about 8 mg/mL to about 25 mg/mL and about 10 mg/mL to about 20 mg/mL. The most preferred peptide concentration is about 15 mg/mL.

Preferably, an aqueous alkaline solution comprising only water and a base such as NaOH, KOH or ammonium hydroxide is employed to dissolve the peptide. A more preferred base is NaOH.

Preferably, the pH of the alkaline normalization step is about 10.0 to about 11.0. More preferably, the pH is about 10.5. The alkaline solution comprising the dissolved peptide may be allowed to sit quiescently for a period of about 5 minutes to about 3 hours at ambient temperature, which, although it is not to be construed as a limitation, is generally between about 20° C. and about 25° C. The alkaline solution may also be gently stirred. More preferably, the dissolved alkaline peptide solution will sit quiescently for about 1 hour at ambient temperature. One skilled in the art will recognize that combinations of pH, time, temperature and stirring conditions for this step can be readily established for each peptide that ensures "normalization" of the peptide conformation is complete yet avoids or minimizes chemical degradation that may occur to the peptide.

The next step in the process for preparing crystals of a selected peptide is the addition of glycine. Amino acids such as glycine bind zinc ions which also bind very tightly to the histidine residue(s) in a peptide. Thus, competition for zinc binding may play a role in the formation of peptide crystals, as well as in the stability of subsequent crystalline compositions. The glycine added to the alkaline peptide solution may be in a solid form or in a stock solution. Preferably, glycine is added as a solid. Preferably, the added glycine is in free-base form. Preferably, the resulting concentration of glycine in the alkaline peptide solution is about 5 mM to about 250 mM. Ranges of more preferred glycine concentration are about 10 mM to about 150 mM, about 20 mM to about 100 mM, about 40 mM to about 80 mM and about 55 mM to about 65 mM. Most preferably, the glycine concentration is about 60 mM.

Optionally, the pH of the alkaline peptide solution may be readjusted after the addition of the glycine. If the pH is adjusted, it is preferably adjusted to a pH between about 9.0 and about 11.0. More preferably, it is adjusted to a pH between about 9.2 and about 9.8. Most preferably, it is adjusted to about pH 9.5.

Optionally, the alkaline peptide solution with added glycine may be filtered. Filtration is recommended if any evidence of undissolved particles, dust or lint is apparent in the solution. If desired, this is also a good place in the process at which the solution can be sterilized by performing an aseptic filtration step. Preferably, the filtration will be conducted using a sterile non-pyrogenic filter having low-protein binding and a pore size of 0.45 μm or less. Preferably, the filter is a sterile non-pyrogenic, low-protein binding filter of pore size 0.22 μm or less. More preferably, the filter is a sterile 0.22 μm Millex® filter (Millipore Corporation, Waltham, Mass., USA).

The next step in the process is addition to the alkaline peptide solution of about 2% to about 20% of the total final volume of an alcohol selected from the group consisting of ethanol and isopropanol, and about 0.2 moles to about 2.5 moles of zinc per mole of the peptide. The zinc and ethanol may be added in a single aqueous stock solution or may be added separately in one or more steps in any order. Preferably, the alcohol is added before the zinc is added.

Preferably, the added alcohol represents, by volume, about 2% to about 20% of the total final volume of the alkaline peptide-zinc-alcohol solution. More preferably, the alcohol represents about 5% to about 15% of the total final volume. More preferably, the alcohol represents about 6% to about 12% of the total final volume. Most preferably, the alcohol represents about 9% of the total final volume. Preferably, the alcohol is ethanol.

The zinc added at this stage refers to the zinc ion. The zinc may be added in a variety of forms, but a zinc oxide solution acidified with dilute HCl and salt forms such as zinc acetate or zinc chloride are preferred. More preferred is a zinc oxide solution acidified with dilute HCl.

Preferably, 1.0 moles to about 2.25 moles of zinc per mole of the peptide is added in this process step. Other preferred ranges of zinc addition include 1.1 to 2.0 moles of zinc per mole of the peptide, 1.3 to 1.7 moles per mole of peptide, and 1.4 to 1.6 moles per mole of peptide. Most preferably, about 1.5 moles of zinc per mole of peptide is added.

Preferably, the solution comprising zinc that is added to the peptide solution is added slowly and/or in small increments, which minimizes the localized precipitation of peptide and/or zinc complexes that may form at the site of addition. More preferably, glycine is also a component of the solution comprising zinc that is being added at this step. For example, a zinc-glycine solution may be prepared by dissolving zinc oxide in dilute HCl to a pH of about 1.6 and then adding solid glycine. A sufficient quantity of glycine is added to raise the pH of the solution to between about pH 2 and about pH 3. The pH of the zinc-glycine solution may be raised further using, for example, dilute NaOH. A preferred pH range of the zinc-glycine solution is about pH 4.0 to about pH 6.0. A more preferred pH range of the zinc-glycine solution is about pH 5.0 to about pH 5.5. As noted earlier, glycine has a binding affinity for zinc that may compete with zinc binding to the peptide. Thus, the presence of glycine in the solution comprising zinc that is being added to the composition allows the zinc solution to be added more quickly because localized precipitation problems are minimized. In addition, having a zinc-glycine solution above pH 2.0, and preferably about pH 4.0 to about pH 6.0, allows the solution to be sterile filtered using filters that are rated by their manufacturers to handle, for example, pH 2–10 solutions, prior to its introduction into a sterile peptide composition. Preferably, the zinc-glycine solution comprises about 50 mM to about 70 mM glycine and about 20 mM to about 200 mM zinc.

The last steps in the initial crystallization of a selected peptide are adjusting the pH of the solution to between about pH 7.5 and about pH 10.5 and allowing crystals of the peptide to form. Preferred reagent solutions useful for adjusting the pH of the solution include dilute HCl, dilute acetic acid and dilute NaOH.

Preferred pH ranges for crystallization of selected peptides include about pH 8.0 to about pH 10.0, about pH 7.5 to about pH 9.5, about pH 8.5 to about pH 9.2, about pH 9.0 to about pH 9.5, about pH 7.5 to about pH 8.5, about pH 8.7 to about pH 9.5, and about pH 9.2 to about pH 10.0.

One skilled in the art will recognize that the preferred pH of crystallization will depend on many factors, including the concentration of peptide, the alcohol concentration, the zinc concentration, the ionic strength of the solution and the temperature of crystallization.

The skilled artisan will further recognize that, for a given set of conditions, a preferred manner of determining the optimal pH of crystallization is to determine it empirically, that is, to slowly add the acidification solution, preferably dilute HCl or dilute acetic acid, in small increments, and observe what happens after each increment is added. Generally, small quantities of localized zones of precipitation will occur at the spot of addition of the acidic solution. When gentle swirling takes increasingly longer periods of time to completely redissolve the precipitation, that is the best time to stop adding the acid and allow crystallization from the clear or slightly cloudy solution to proceed.

The skilled artisan will further recognize that the pH and temperature that one selects for crystallization will have an impact on the speed at which the crystallization proceeds, the crystallization yield, and the size and homogeneity of the crystals formed. Preferably, the pH of crystallization for the selected peptides is about pH 8.0 to about pH 10. More preferably, the pH is about 8.7 to about 9.5. Other ranges of preferred pH of crystallization are about 8.8 to about 9.3, about 9.0 to about 9.5, and about 8.5 to about 9.3. Most preferably, the crystallization is conducted at about pH 9.1.

Preferably, the temperature of crystallization is about 10° C. to about 30° C. More preferably, the temperature of crystallization is about 15° C. to about 28° C. Most preferably, the temperature of crystallization is ambient temperature, or about 20° C. to about 25° C.

Preferably, the crystallization step described above is complete, that is, 90% or more of the peptide is precipitated in predominantly crystalline form, in about 3 hours to about 72 hours. More preferably, the crystallization is complete in about 10 hours to about 48 hours. Most preferably, the crystallization is complete in about 16 hours to about 26 hours. Completion of crystallization may be determined by a variety of means, including HPLC analysis of the peptide present in an aliquot of the composition. Method 5 herein describes one such protocol that may be employed.

Preferably, the crystals produced according to the steps of the process described above are thin plate crystals. The crystals produced by the process may be examined by microscopy.

Pharmaceutical compositions comprising crystals of a peptide prepared as described above may be prepared by adding suitable, pharmaceutically acceptable excipients to the crystal suspension in the original mother liquor. Alternatively, the crystals may be isolated by filtration, gentle centrifugation or other means of phase separation, and used in a variety of ways to prepare pharmaceutically acceptable compositions. The skilled artisan will recognize suitable procedures and excipients useful for preparing such pharmaceutical compositions.

To prepare a stable pharmaceutical composition of crystals of a selected peptide, the pH of the suspension of crystals in their complete original mother liquor, or portion thereof, is lowered to a pH value at which 97% or more of the peptide becomes insoluble. Preferably, this part of the process begins within a few hours after the initial crystallization is determined to be complete. Preferably, the pH is lowered using a dilute solution of HCl or acetic acid wherein the acidic solution is added slowly and in incremental portions. The skilled artisan will recognize that the preferred pH at which this second stage of crystallization should occur will depend on many factors, including the nature of the peptide and its concentration, the alcohol concentration, the zinc concentration, the ionic strength of the suspension and the temperature of crystallization. Preferably, the pH is about 0.2 to 2.0 pH units lower than the pH at which the initial crystallization proceeded. More preferably, the pH is about 0.5 to about 1.5 pH units lower, and most preferably, the pH is about 0.8 to 1.3 pH units lower than the pH at which the initial crystallization proceeded. The temperature of this second stage of crystallization is preferably ambient temperature, or about 20° C. to about 25° C. For the peptide $Val^8$-GLP-1(7–37)OH, a preferred pH is about 7.5 to about 8.5. A more preferred pH is about 7.8 to about 8.2.

Preferably, the pH of a suspension of peptide crystals is lowered to a pH at which 98% or more, and more preferably at which 99% or more of the peptide becomes insoluble in the composition. The additional precipitation formed in this second stage of crystallization comprises crystals. Preferably, the additional precipitation formed in this second stage of crystallization will be predominantly crystals of comparable morphology and size distribution as those formed in the first stage of crystallization.

Preferably, the second stage of crystallization is complete enough, that is, 97% or more of the peptide is insoluble, to allow the following step to begin within 30 hours, more preferably within 18 hours, more preferably within 6 hours and most preferably within 2 hours of when the second stage of crystallization started. Quantitation of precipitation yield may be determined by a variety of means, including HPLC analysis of the peptide present in an aliquot of the composition. Method 5 herein describes one such protocol that may be employed.

The next step in the process to prepare a stable pharmaceutical composition of crystals of a selected peptide is to add a pharmaceutically acceptable preservative and buffer selected from the group consisting of TRIS and maleate. Optionally, one or more tonicity agents such as sodium chloride, other salts, glycerin or mannitol may also be added. These components may be added as a single solution, as combination solutions or individually in any order. It is preferred that the preservative is added last. Of these components, a preferred buffer is selected from the group consisting of TRIS and maleate, a preferred preservative is m-cresol and a preferred tonicity agent is sodium chloride. A more preferred buffer is TRIS.

A preferred quantity of TRIS to add to the crystalline peptide suspension, if TRIS is the selected buffer, is such that the TRIS concentration in the final composition is about 5 mM to about 40 mM. A more preferred range of TRIS concentration in the final composition is about 10 mM to about 20 mM. A most preferred concentration of TRIS in the final composition is about 15 mM.

A preferred quantity of maleate to add to the crystalline peptide suspension, if maleate is the selected buffer, is such that the maleate concentration in the final composition is about 2 mM to about 20 mM. A more preferred range of maleate concentration in the final composition is about 5 mM to about 15 mM. A most preferred concentration of maleate in the final composition is about 9 mM.

If sodium chloride is selected to be a component of a peptide composition of the present invention, a preferred quantity to add to the crystalline peptide suspension is such that the added sodium chloride in the final composition is about 30 mM to about 200 mM. A more preferred concentration of added sodium chloride in the final composition is 50 mM to about 150 mM. Other ranges of preferred sodium chloride concentration are about 80 mM to about 120 mM, about 70 mM to about 130 mM, and about 90 mM to about 130 mM. A most preferred quantity of added sodium chloride in a pharmaceutical composition of the present invention is about 110 mM.

Although any pharmaceutically acceptable preservative may be added to the crystalline peptide suspension at this point in the process, for a composition of the present invention a phenolic preservative or benzyl alcohol is preferred. Examples of phenolic preservatives include phenol, chlorocresol, m-cresol, o-cresol, p-cresol, ethylparaben, methylparaben, propylparaben, butylparaben, thymol or mixtures thereof. More preferred preservatives are benzyl alcohol, m-cresol, phenol, methylparaben and mixtures thereof. A most preferred pharmaceutically acceptable preservative is m-cresol.

A preferred quantity of a pharmaceutically acceptable preservative to add to a crystalline peptide composition at this point in the process is an amount such that the preservative concentration in the final composition is about 1.0 mg/mL to about 20.0 mg/mL. More preferred ranges of concentration of preservative in the final composition are about 2.0 mg/mL to about 8.0 mg/mL, about 2.5 mg/mL to about 4.5 mg/mL and about 2.0 mg/mL to about 4.0 mg/mL. A most preferred concentration of preservative in the final composition is about 3.0 mg/mL.

The final step in the process of preparing a stable pharmaceutical composition of crystals of a selected peptide is an adjustment to a final pH between about 6.0 and about 8.5, and preferably between about pH 6.5 and about pH 8.0, and more preferably between about pH 7.0 and about pH 8.0. Although any of a wide variety of acidification and/or alkalization reagent solutions may be employed for this pH adjustment, dilute HCl, dilute NaOH and dilute acetic acid are preferred. More preferred reagent solutions are dilute HCl and dilute NaOH. The preferred pH to which the composition is adjusted will depend to some extent upon the selected peptide, the peptide concentration, the proposed route of administration and the selected buffer.

Preferably, with TRIS as the selected buffer, the pH will be adjusted to a pH between about 6.5 and about 8.5. More preferably, the pH will be adjusted to a pH between about 7.0 and about 7.8, between about 7.2 and about 7.8, between about 7.5 and about 8.5, or between about 7.0 and about 8.0. A most preferred pH to which the composition is adjusted when TRIS is the selected buffer is about 7.5. With maleate as the selected buffer, the pH will be adjusted to a pH between about 6.0 and about 7.5. More preferably, the pH will be adjusted to a pH between about 6.4 and about 7.5, between about 6.4 and about 7.0, or between about 6.0 and about 7.0. A most preferred pH to which the composition is adjusted when maleate is the selected buffer is about 6.5.

Another aspect of the present invention is a stable pharmaceutical composition prepared by the process described in the preceding paragraphs.

Method 1

Sedimentation Rate

Cartridges or vials containing a suspension of crystals are evaluated visually for crystal settling rate and volume. After thoroughly suspending the insoluble material in the cartridges or vials, each composition is allowed to settle quiescently at ambient temperature (about 20° C. to about 25° C.). The resulting sedimentation volume of the suspended material in each of the compositions after 1 hour is determined as a percentage of total volume. Further, after sitting quiescently for 24 hours at ambient temperature, the sedimentation volume for each sample is determined as a percentage of total volume.

Method 2

TCR Test

The TCR (temperature cycling and resuspension) Test is an automated procedure combining temperature cycling from 25° C. to 37° C. and mechanical agitation that evaluates formulations under conditions more extreme than would be expected for patient usage. This test was described for insulin suspensions and solutions by Shnek, D. R. et al., in J. Pharmaceutical Sciences 87:1459–1465 (1998).

Briefly, the TCR Test employs temperature cycling between 25° C. and 37° C. in an incubator unit combined with resuspensions conducted twice daily on a mechanical device outside the incubator unit. The 3-mL glass cartridges containing a 1 mm glass bead and rubber plunger are filled with peptide suspensions and capped with a disk seal. The samples are held in a horizontal position for 10 hours per day at 25° C. and 10 hours per day at 37° C., with 2-hour temperature ramping steps between them. The mechanical resuspension of the test cartridges performs three sets of 10 lateral rolls plus 10 cartridge inversions twice daily. The resuspensions are conducted during the 25° C. temperature cycle. The entire test lasts up to 28 days. For additional details of the TCR Test see Shnek, D. R. et al., supra.

Method 3

Modified TCR Test

The Modified TCR Test is similar to the TCR Test described in Method 1 except that the temperature cycles are 5° C. and 25° C. The resuspensions are conducted during the 25° C. cycle.

Method 4

Particle Size Measurements

Particle size measurements are performed using a Coulter Model LS230 Particle Size Analyzer (Beckman Coulter, Inc., Fullerton, Calif., USA). An aliquot (about 100 µL) of the test suspension is diluted about 100-fold to about 300-fold by pipetting it into a diluent containing 2.4 mM zinc, 150 mM NaCl and 50 mM sodium acetate at pH 5. Particle size data are collected for about 120 seconds, and the resulting distribution is analyzed with Coulter particle size statistics software which assumed a spherical shape. The mean volume percent distribution of particle sizes is obtained and reported.

Method 5

Visual Assessment of Peptide Compositions

Cartridges of peptide suspension compositions being evaluated in the TCR Test and in the Modified TCR Test are examined by trained operators on various test days. The test compositions are checked for visual changes compared to quiescently refrigerated control samples. Visual changes included the presence of large aggregates (also designated as clumps) and/or material that adheres to the cartridge wall (also designated as frosting). For the evaluation of test results, a milky white suspension or the presence of grainy material that resuspends upon swirling is reported as PASS while visual changes involving large-aggregates, clumps, frosting, or grainy material that does not resuspend upon swirling is reported as FAILED. Additional details of these evaluation criteria are described in Shnek, D. R. et al., supra.

Method 6

HPLC Analysis of Peptides

Peptides in the aqueous compositions of the present invention are analyzed on a 25 cm×4.6 mm Zorbax 300 SB (C-8) HPLC column (Mac-Mod Analytical Inc., Chadds Ford, Pa., USA) with UV detection at 214 nm. A gradient made from a first solution (0.1% TFA in water) and a second solution (0.1% TFA in acetonitrile) is used to effect elution of the peptides and related impurities.

Method 5 is used to determine the purity of peptides in suspensions undergoing the TCR Test (Method 2) and the Modified TCR Test (Method 3). For these analyses, an aliquot of the suspended composition is diluted about 10-fold or greater with a 2 M guanidine-0.01 N HCl solution to solubilize the peptide crystals prior to injection.

To quantitate the soluble peptide present in a suspension composition, portions of the swirled suspension are centrifuged and an aliquot of the clear supernatant is analyzed by HPLC as described above.

Method 7

FTIR Analysis

FTIR (Fourier Transform Infrared Raman) spectra are acquired on a Nicolet Nic-Plan FTIR microscope using a Nicolet 760 Spectrometer optical bench (Nicolet Instrument Corporation, Madison, Wis., USA) and Omnic version 5.1 software. Microliter portions of the peptide samples are placed on a glass slide and allowed to evaporate to dryness in a desiccator overnight at ambient temperature (20° C. to 25° C.). The dried peptide is removed from the slide using a micro-tool and placed on a diamond anvil cell (Spectra-Tech, Inc., Shelton, Conn., USA) for analysis. Spectra were acquired at 4 $cm^{-1}$ resolution from 128 scans and are baseline adjusted. The background spectra are similarly obtained with half of the diamond anvil cell in the beam. For analysis of secondary structure, second derivatives and deconvolved spectra are obtained using Nicolet software. Second derivatives are inverted (multiplied by −1000) and smoothed (11 points over 10.6 $cm^{-1}$). Deconvolved spectra are obtained using a 23 $cm^{-1}$ bandwidth and 2.2 enhancement factor.

The following examples are provided merely to further illustrate the invention. The scope of the invention shall not be construed as merely consisting of the following examples.

EXAMPLE 1

Chemical Synthesis of $Val^8$-GLP-1(7–37)$NH_2$

Peptides are prepared by the solid-phase method of Merrifield et al. (1963) *J. Am. Chem. Soc.* 85:2149–2154 either by the original t-Butyloxycarbonyl/Benzyl (t-Boc/Bzl) methodology or fluroenyloxycarbonyl/t-Butyl (Fmoc/tBu) based method.

t-Boc/Bzl Synthesis:

The synthesis is initiated with 4-methylbenzhydrylamine (4-MBHA) derivatized polystyrene resin which is used to anchor the $1^{st}$ residue, t-Boc protected glycinamide. The synthesis can be carried out manually (on variable scale) or by automated stepwise fashion using a peptide synthesizer (typically 0.25 mmole scale). Boc group deprotection is carried out by treatment with trifluoroacetic acid, the free N-terminus is neutralized with diisopropylethylamine either prior to or simultaneously with the next coupling. Boc protected amino acids are activated with DIC (diisopropylcarbodiimide) or DCC (dicyclohexylcarbodiimide) to form symmetrical anhydrides or with HBTU (hydroxybenztriazolyl tetramethyluronium hexafluorophosphate) to form activated esters. This deprotection-neutralization-coupling cycle is repeated until the peptide sequence is fully assembled. Conventional side chain protection is as follows: Arg(Tosyl), Asp(cHexyl) Gln(Xanthyl), Glu(cHexyl) His (Boc), Lys(2-ClBenzyl), Ser(Benzyl), Thr (Benzyl), Trp (formyl), Tyr(2-BrBenzyl). The protected peptide is simultaneously cleaved from the support and deprotected using liquid hydrogen fluoride containing an appropriate scavenger such as cresol or m-cresol. The peptide is precipitated with diethyl ether, purified by high performance liquid chromatography and lyophilized.

Fmoc/tBu Synthesis:

The synthesis is initiated with 2,4-dimethoxy-benzhydrylamine ("Rink" type) polystyrene resin which is used to anchor the $1^{st}$ residue, Fmoc protected glycinamide. Again, the synthesis can be carried out manually (on variable scale) or by automated stepwise fashion using a peptide synthesizer (typically 0.25 mmole scale). Fmoc group deprotection is carried out by treatment with piperidine in dimethylformamide. Fmoc protected amino acids are activated with DIC (diisopropylcarbodiimide) or DCC (dicyclohexylcarbodiimide) to form symmetrical anhydrides or with HBTU (hydroxybenztriazolyl tetramethyluronium hexafluorophosphate) to form activated esters. This deprotection-coupling cycle is repeated until the peptide sequence is fully assembled. Conventional side chain protection is as follows: Arg(pentamethylbenzofuran), Asp(O-tButyl), Gln(trityl), Glu(O-tButyl) His(t-Butyloxycarbonyl), Lys(t-Butyloxycarbonyl), Ser(O-tButyl), Thr(O-tButyl), Trp(t-butyloxycarbonyl), Tyr(O-tButyl). The protected peptide is simultaneously cleaved from the support and deprotected using trifluoroacetic acid containing an appropriate scavenger such as ethanedithiol and water. The cleavage mixture is concentrated, the peptide precipitated with diethyl ether. The crude peptide is purified by high performance liquid chromatography and lyophilized.

EXAMPLE 2

Trypsin Mediated Transpeptidation $Val^8$GLP-1(7–37)OH to $Val^8$-GLP-1(7–37)$NH_2$ $Val^8$-GLP-1(7–37)OH, is converted to the $Val^8$-GLP-1(7–37)$NH_2$ using trypsin mediated transpeptidation to remove the C-terminal glycine residue and replace with a glycinamide residue. Trypsin is used because of its selectivity for basic amino acid residues (lysine, arginine) and that the penultimate amino acid residue at the C-terminal end of $Val^8$-GLP-1(7–37)OH is arginine. To prevent trypsin digesting the $Val^8$-GLP(7–37)OH at each of the two lysine the $Val^8$-GLP-1(7–37)OH is treated with an excess of citriconic anhydride in an aqueous buffered solution (pH 9–10) to temporarily protect the lysine residues and render them "invisible" to trypsin. This also caps the N-terminal amino group of $Val^8$-GLP-1(7–37)OH. Next, the excess citriconic anhydride is quenched with ethanolamine. Then trypsin is added (1:10 vs. $Val^8$GLP-1(7–37)OH on a weight basis) from its stock solution (50 mM calcium acetate in water) under constant stirring (pH 8–9). This converts the $Val^8$-GLP-1(7–37)OH to the $Val^8$-GLP-1(7–36)OH by removing the C-terminal glycine residue. After thirty minutes of digestion a 50 fold molar excess of glycinamide hydrochloride suspended in dimethylacetamide (volume calculated to result in a 35/65% (v/v) aqueous/organic solution (pH~8–9)). The reaction mixture is then placed on a stir plate in a refrigerator at 4 degrees centigrade and the conversion monitored by analytical reversed-phase HPLC and mass spectra.

Removal of citriconyl groups for HPLC analysis is effected by incubating a 10-fold diluted sample (in 0.1 M H3PO4/6M GdnHCl) at 110 degrees centigrade for 10 minutes.

EXAMPLE 3

Aggregation Time $Val^8$-GLP-1(7–37)OH and $Val^8$-GLP-1(7–37)$NH_2$ $Val^8$-GLP-1(7–37)OH and $Val^8$-GLP-1(7–37)$NH_2$ were analyzed with respect to their potential to aggregate in solution. In general, the peptides in solution were stirred at elevated temperature in a suitable buffer while recording turbidity at 350 nm as a function of time. Time to the onset of aggregation was measured to quantify the potential of a given GLP molecule to aggregate under these stressed conditions.

The GLP-1 peptides were first dissolved under alkaline conditions (pH 10.5) for 30 minutes to dissolve any pre-aggregated material. The solution was then adjusted to pH 7.4 and filtered. Specifically, 4 mg of a lyophilized GLP-1 peptide was dissolved in 3 mL of 10 mM phosphate/10 mM citrate. The pH was adjusted to 10.0–10.5 and held for 30 minutes. The solution was adjusted with HCl to pH 7.4 and filtered through a suitable filter, for example a Millex® GV syringe filter (Millipore Corporation, Bedford, Mass.). This solution was then diluted to a final sample containing 0.3 mg/mL protein in 10 mM citrate, 10 mM phosphate, 150 mM NaCl, and adjusted to pH 7.4 to 7.5. The sample was incubated at 37° C. in a quartz cuvette. Every five minutes the turbidity of the solution was measured at 350 nm on an AVIV Model 14DS UV-VIS spectrophotometer (Lakewood, N.J.). For 30 seconds prior to and during the measurement the solution was stirred using a magnetic stir bar from Starna Cells, Inc. (Atascadero, Calif.). An increase in OD at 350 nm indicates aggregation of the GLP-peptide. The time to aggregation was approximated by the intersection of linear fits to the pre-growth and growth phase according to method of Drake (Arvinte T, Cudd A, and Drake A F. (1993) *J. Bio. Chem.* 268, 6415–6422)

The cuvette was cleaned between experiments with a caustic soap solution (e.g., Contrad-70).

$Val^8$-GLP-1(7–37)OH aggregated in approximately 1.5 hours at 30° C. and approximately 1 hour at 37° C. $Val^8$-GLP-1(7–37)$NH_2$ showed a substantially reduced tendency to aggregate. $Val^8$-GLP-1(7–37)$NH_2$ did not aggregate for approximately 23 hours at 37° C.

EXAMPLE 4

In Vitro Activity $Val^8$-GLP-1(7–37)$NH_2$ relative to $Val^8$-GLP-1(7–37)OH

HEK-293 Aurora CRE-BLAM cells expressing the human GLP-1 receptor are seeded at 20,000 to 40,000 cells/well/100 µl into a 96 well black clear bottom plate. The day after seeding, the medium is replaced with plasma free medium. On the third day after seeding, 20 µL of plasma free medium containing different concentrations of GLP-1 peptide is added to each well to generate a dose response curve. Generally, fourteen dilutions containing from 3 nm to 30 nm GLP-1 peptide were used to generate a dose response curve from which EC50 values could be determined. After 5 hours of incubation with GLP-1 peptide, 20 µL of β-lactamase substrate (CCF2-AM—Aurora Biosciences—product code 100012) was added and incubation continued for 1 hour at which point the fluorescence was determined on a cytofluor. The in vitro activity of $Val^8$-GLP-1(7–37)$NH_2$ relative to the in vitro activity of $Val^8$-GLP-1(7–37)OH for 7 different samples is illustrated in Table 2 below.

TABLE 2

| Sample # | $Val^8$-GLP-1(7–37)$NH_2$ (% $Val^8$-GLP-1(7–37)OH) |
|---|---|
| 1 | 150 |
| 2 | 106 |
| 3 | 128 |
| 4 | 125 |
| 5 | 133 |
| 6 | 92 |
| 7 | 79 |

Avg = 116%

EXAMPLE 5

Crystallization of Val$^8$-GLP-1(7–37)NH$_2$

Val$^8$-GLP-1(7–37)NH$_2$ was dissolved in about 0.48 mL of 0.015 N NaOH at a concentration of about 17 mg/mL, based on the mass of the peptide. The protein solution was adjusted to about pH 11.1 with dilute NaOH, then to pH 10.36 with dilute HCl. The solution was held at ambient temperature for about 1 hour.

To a 390 µL aliquot of this peptide solution was added 25 µL of a 1.0 M glycine pH 10 solution, giving a final concentration of about 16 mg/mL of Val$^8$-GLP-1(7–37)NH$_2$ and about 60 mM glycine.

The solution was then filtered into a glass vial through a sterile 0.22 µm Millex®-GV (Millipore Corporation, Waltham, Mass., USA) 4 mm filter unit.

To 300 µL of the filtered peptide solution in a clean glass vial was added 66 µL of a 50% ethanol solution in water. To this solution was added, in small increments, a total of about 7 µL of a 150 mM zinc oxide pH 2.3 solution (prepared with dilute HCl), with mixing by hand performed after each increment was added until the solution became clear. The molar ratio of zinc:peptide was about 0.75:1.

The final solution was adjusted to about pH 9.8 and crystallization proceeded at ambient temperature. The crystallization solution comprised about 12.6 mg/mL Val$^8$-GLP-1(7–37)NH$_2$, 47 mM glycine, 8.7% ethanol by volume, and about 0.75 moles of zinc per mole of Val$^8$-GLP-1(7 37)NH$_2$ at pH 9.8.

After about 48 hours at ambient temperature, clusters of Val$^8$-GLP-1(7–37)NH$_2$ were observed under a microscope at 400× magnification.

---

We claim:

1. A peptide consisting of the sequence of Formula I (SEQ ID NO: 1):

```
                        Formula I (SEQ ID NO: 1)
 7   8   9  10  11  12  13  14  15  16  17
His-Xaa-Glu-Gly-Thr-Phe-Thr-Ser-Asp-Val-Ser- 18  19  20  21  22  23  24  25  26  27  28
Ser-Tyr-Leu-Glu-Xaa-Gln-Ala-Ala-Lys-Xaa-Phe- 29  30  31  32  33  34  35  36  37
Ile-Xaa-Trp-Leu-Val-Lys-Gly-Arg-R
``` wherein:
Xaa at position 8 is Val;
Xaa at position 22 is Gly;
Xaa at position 27 is Glu;
Xaa at position 30 is Ala; and
R is Gly-NH$_2$.

* * * * *